| United States Patent [19] | [11] Patent Number: 4,987,077 |
|---|---|
| Charnley et al. | [45] Date of Patent: Jan. 22, 1991 |

[54] PREPARATIONS OF PROTEASE ENZYMES DERIVED FROM ENTOMOPATHOGENIC FUNGI

[75] Inventors: Anthony K. Charnley, Avon; Richard M. Cooper, Corsham, both of England; Raymond J. St. Leger, Ithaca, N.Y.

[73] Assignee: Agricultural Genetics Company Limited, Cambridge, England

[21] Appl. No.: 197,970

[22] Filed: May 24, 1988

[30] Foreign Application Priority Data

Mar. 30, 1988 [JP] Japan .................................. 63-77966
Mar. 31, 1988 [EP] European Pat. Off. ........ 88302907.6

[51] Int. Cl.⁵ ...................... C12N 09/58; C12N 09/48; C12N 01/14; C12N 01/00
[52] U.S. Cl. .................................. 435/223; 435/212; 435/911; 435/254
[58] Field of Search .................... 435/212, 223, 911

[56] References Cited

U.S. PATENT DOCUMENTS 2,927,060  3/1960  Oringer ............................. 435/223
2,936,265  5/1960  Whitehill et al. .................. 435/223

OTHER PUBLICATIONS

Leger et al., *Archives of Biochemistry and Biophysics*, vol. 253, pp. 221–232 (1987).
Leger et al., *Archives of Biochemistry and Biophysics*, vol. 258, pp. 123–131 (1987) (First Page).
*J. Invertebrate Pathology*, vol. 35, pp. 304–310 (1980).
Search Report for European Patent Application 88 302907-6.
*J. Invertebrate Pathology*, vol. 47, pp. 167–177 (1986).
*J. Invertebrate Pathology*, vol. 48, pp. 85–95 (1986).
*Applied and Environmental Microbiology*, vol. 53, pp. 1679–1684.

*Primary Examiner*—Elizabeth C. Weimar
*Assistant Examiner*—Eric J. Kraus
*Attorney, Agent, or Firm*—Oblon, Spivak, McClelland, Maier & Neustadt

[57] ABSTRACT

The invention provides an enzyme preparation comprising at least one protease derived from an entomopathogenic fungus of one of the following genera: Metarhizium, Beauvaria, Verticillium, and Aschersonia, and characterized by the following properties:
(a) substantially not activity against hide protein azure, locust cuticel and elastin;
(b) specificity for Bz-Phe-Val-ARg-NA;
(c) not inhibited by soybean trypsin inhibitor.

3 Claims, No Drawings

PREPARATIONS OF PROTEASE ENZYMES DERIVED FROM ENTOMOPATHOGENIC FUNGI

This invention relates to fungal enzymes and more particularly to highly specific proteases produced by entomopathogenic fungi.

The entomopathogenic fungus *Metarhizium anisopliae* (isolate ME1) has been shown to produce a mixture of extracellular proteases (R. J. St. Leger, A. K. Charnley and R. M. Cooper, Characterization of cuticle-degrading proteases produced by the entomopathogen *Metarhizium anisopliae* MEI, Archives of Biochemistry and Biophysics (1987) 253, 221-232). The proteases have been resolved into two major components; chymoelastase (designated Pr1) and a trypsin-like protease (designated Pr2); isoenzymes of Pr2 are present.

Pr1 has a broad substrate specificity but Pr2 has a much narrower substrate range. Although Pr2 rapidly hydrolyses casein and synthetic substrates containing arginine or lysine it has little or no activity against host insect cuticle, elastin, or synthetic substrates for chymotrypsin and elastase. Specific active site inhibitors confirmed the similarities between Pr2 and trypsin.

A further 8 isolates of the entomopathogenic fungi *M. anisopliae* (4 isolates), *Beauvaria bassiana*, *Verticillium lecanii* (2 isolates), and *Aschersonia alevrodis* have been screened for extracellular proteases. All the isolates produce Pr1 and Pr2 proteases but, surprisingly, the Pr2 proteases of 6 of these isolates have a very narrow substrate specificity when compared to the previously described Pr2 protease of *M. anisopliae* (ME1).

The Pr2 proteases of *M. anisooliae* isolates ME1, RS549 and RS23 are active against hide protein azur but not against locust cuticle and elastin (table 1). In contrast, Pr2 proteases from the other 6 isolates are inactive against all three proteins. Further evidence of the restricted substrate specificity of the Pr2 proteases from the other 6 isolates was obtained from studies on artificial substrates (nitroanilide derivatives of peptides). Pr2 enzymes from MEI, RS549 and RS23 hydrolysed a series of substrates Bz-AA-AA-Arg-NA thus demonstrating little discrimination in their secondary subsite specificities (table 2, see below). In contrast, the Pr2 proteases from the other 6 isolates showed a specificity for Bz-Phe-Val-Arg-NA. Thus these enzymes require extremely specific substrate sequences and as such they represent a previously unreported class of fungal protease. The only other enzymes reported with similar restricted specifities are certain thrombins such as Thrombocytin (from Bothroos atox venom). Thrombocytin rapidly cleaves Bz-Phe-Val-Arg-NA with minor activity against Bz-Pro-Phe-Arg-NA.

Further differences between the Pr2 proteases from MEI, RS549 and RS23, and those from the other 6 isolates were revealed by inhibitor studies (table 3, see below). Pr2 proteases from MEI, RS549 and RS23, like thrombocytin, are inhibited by soyabean trypsin inhibitor whereas Pr2 proteases from the other 6 isolates (except *A. alevrodis* which was not tested) are not inhibited.

Such highly specific proteases may have useful pharmaceutical, agricultural or industrial applications.

The present invention thus provides an enzyme preparation comprising at least one protease derived from an entomopathogenic fungus of one of the following genera: *Metarhizium*, *Beauvaria*, *Verticillium*, and *Aschersonia*, and characterized by the following properties:

(a) substantially no activity against hide protein azure, locust cuticle and elastin;
(b) specificity for Bz-Phe-Val-Arg-NA;
(c) not inhibited by soybean trypsin inhibitor.

In a preferred aspect, the protease is derived from one of the following species: *Metarhizium anisopliae*, *Beauvaria bassiana*, *Verticillium lecanii*, and *Aschersonia alevrodis*.

In a particularly preferred aspect, the protease is derived from one of the following strains, or a derivative or mutant thereof capable of producing said protease. These strains have been deposited at the Commonwealth Mycological Institute (CMI), Ferry Lane, Kew, Richmond, Surrey, TW9 3AF, U. K. on 12 Oct. 1987 and have the following culture collection numbers:

| Microorganism | CMI CC Number |
| --- | --- |
| *Metarhizium anisopliae* var major RS 324 | 319793 |
| *Metarhizium anisopliae* var major RS 298 | 319794 |
| *Verticillium lecanii* 1 | 319795 |
| *Verticillium lecanii* 2 | 319796 |
| *Beauveria bassiana* | 319797 |
| *Aschersonia aleyrodis* | 319798 |

The characteristics of the deposited strains referred to above essentially correspond to the description of typed strains which have been published.

The invention is illustrated by the following Examples.

| Abbreviations | |
| --- | --- |
| Bz-AA-AA-Arg-NA: | N-benzoyl-L-aminoacid-L-aminoacid-L-arginine-p-nitroanilide. |
| Bz-Phe-Val-Arg-NA: | N-benzoyl-L-phenylalanine-L-valine-L-arginie-p-nitroanilide. |
| Bz-Val-Gly-Arg-NA | N-benzoyl-L-valine-glycine-L-arginine-p-nitroanilide. |
| Bz-Pro-Phe-Arg-NA: | N-benzoyl-L-proline-L-phenylalanine-L-arginine-p-nitroanilide. |
| CBZ-Gly-Pro-Arg-NA: | N-carbobenzoxy-glycine-L-proline-L-arginine-p-nitroanilide. |
| Bz-Arg-NA: | N-benzoyl-L-arginine-p-nitroanilide. |
| D-Val-Leu-Lys-NA: | D-valine-L-leucine-L-lysine-p-nitroanilide. |
| Suc-(Ala)2-Pro-Phe-NA: | N-succinyl-L-alanine-L-alanine-L-proline-L-phenylalanine-p-nitroanilide. |
| Suc-Phe-Leu-Phe-NA: | N-succinyl-L-phenylalanine-L-leucine-L-phenylalanine-p-nitroanilide. |
| Suc-(Ala)2-Pro-Leu-NA: | N-succinyl-L-alanine-L-alanine-L-proline-L-leucine-p-nitroanilide. |
| Suc-(Ala)2-Pro-Abu-NA: | N-succinyl-L-alanine-L-alanine-L-proline-L-amino-n-butyric acid-p-nitroanilide. |
| Suc-(Ala)2-Val-Ala-NA: | N-succinyl-L-alanine-L-alanine-L-valine-L-alanine-p-nitroanilide. |
| Ac-(Ala)3-NA: | N-acetyl-L-alanine-L-alanine-L-alanine-p-nitroanilide. |
| PMSF: | Phenylmethylsulphonyl fluoride. |
| Tos-Lys-CH2Cl: | N-p-tosyl-L-lysine-chloromethylketone. |
| Tos-Phe-CH2Cl: | N-tosyl-L-phenylalanine-chloromethylketone. |
| BOC-Gly-Leu-Phe-CH2Cl: | N-tert-butoxycarbonyl-glycine-L-leucine-L-phenylalanine-chloromethylketone. |

EXAMPLES

1. Producer Organisms
    *Metarhizium anisopliae* var. major RS 324

*M. anisopliae* var. major RS 298
*Verticillium lecanii* 1
*V. lecanii* 2
*Beauveria bassiana*
*Aschersonia alevrodis*

2. Growth conditions

The *Metarhizium* and *Verticillium* isolates were maintained on Sabouraud's Dextrose agar at 23° .C (*V. lecanii*) or 27° C. (*M. anisopliae*). The *B. bassiana* isolate was maintained at Czapek-Dox medium at 27° C. The *A. alevrodis* isolate was maintained on Maltose agar at 23° C.

Fungi were grown in 100 ml of growth medium in 250 ml Erlenmeyer flasks. The composition of the growth medium was as follows:

1% w/v carbon source
0.1% w/v $KH_2PO_4$
0.05% w/v $MgSO_4$
0.05 M 4-morpholine ethanesulphonic acid pH6.0
0.2 µg/ml $FeSO_4 \cdot 7H_2O$
1.0 µg/ml $ZnSO_4 \cdot 7H_2O$
0.2 µg/ml $NaMoO_4 \cdot 2H_2O$
0.02 µg/ml $CuSO_4 \cdot 5H_2O$
0.02 µg/ml $MnCl_2 \cdot 4H_2O$ The following polymeric, non-repressing carbon sources can be used: locust cuticle, bovine serum albumen, laminarin, cellulose, elastin, collagen. When cellulose is used, the growth medium must be supplemented with 0.2% w/v $NaNO_3$ as a nitrogen source.

Insoluble carbon sources were added to previously sterilized basal media (121° C., 15 min) and autoclaved for 5 min at 115° C. Soluble carbon sources were autoclaved in basal media for 20 min at 115° C.

After inoculation with $3 \times 10^6$ spores taken from 7-to 12- day agar plates the flasks were shaken on a rotary incubator (150 rev/min) at 23° C. (*V. lecanii, A. alevrodis*) or 27.5° C. (*M. anisopliae* and *B. bassiana*).

3. Purification of enzymes

Cultures grown for 5d (14d with *A. alevrodis*) in 1% locust cuticle basal salts media (200 ml in 500 ml conical flasks rotated at 150 rpm) were clarified by filtration (through Whatman 1 paper) and centrifugation (8,000 g, 15 min at 3° C.). The solid material (cuticle and fungal bodies) was washed in 0.1 M K phosphate buffer (ca. 3% w/v, wet wt) to remove electrostatically bound enzymes, filtered and centrifuged. This filtrate and the original culture filtrate were dialysed separately (4° C., 12h vs $2 \times 300$ vol dist $H_2O$, pH 6.0), concentrated (vs polyethylene glycol M. W. 20,000) and combined (final volume 50 ml) before preparative isoelectric focusing (IEF) as described below. The pH of fractions was determined (the gradient was discontinuous above pH 10.0 so pI values above 10.0 were approximations) and fractions were assayed for enzymatic activity following dialysis against 0.2 M KCI (4° C., 12 h) and then distilled water (4° C., 12 h).

Preparative IEF (pH 3.5-10.0) was performed with a 440 ml (LKB 8100) column. Narrow range IEF was performed in a 110 ml (LKB 8101) column. The procedures were described in the manufacturer's handbook. Enzyme activities and protein levels in the eluate were determined after removal of ampholytes by exhaustive dialysis against 0.2 M KCl (14 h, 4° C., 300 vol) and distilled water (12 h, 4° C., 300 vol) at pH 6.0.

4. Characterization of enzymes a. Assays of enzyme activity

Non-specific protease activity was measured with hide protein azure. 5 ml bottles were charged with 20 mg of substrate, 4 ml of Britton Robinson buffer of required pH, and 1 ml of enzyme. The bottles were stoppered and fastened to a revolving disk. After incubation at 30° C., reactions were terminated by the addition of trichloroacetic acid (0.25 ml, 500 g/liter). After centrifugation (5,000 g, 10 min) absorbance was measured at 595 nm. Activities are expressed as µg trypsin equivalents/ml/hr calculated from a standard curve of trypsin activity against hide protein azure. The results are shown in table 1.

Elastase activity was estimated in a reaction mixture containing 4 ml Tris buffer (0.05 M, pH 8.0), 1 ml of enzyme solution, and elastin - Congo Red (1 mg ml$^{-1}$ protein). After appropriate time intervals at 30° C. the mixtures were centrifuged (5000 g, 10 min) and the absorbance was determined at 450 nm. One elastolytic unit was defined as the amount of enzyme which solubilized 1 mg of elastin in 30 min.

Activity against purified proteins was assayed as follows: 0.5 ml of enzyme solution was incubated with 1.0 ml of 0.05 M Tris buffer (pH 8.0) containing 2.5 mg ml$^{-1}$ protein. After appropriate periods of incubation at 30° C. the reaction was terminated by adding 2 ml of 10% trichloroacetic acid and the tubes were allowed to stand for 1 hour. The residue of undigested protein was removed by filtration through Whatman No. 50 filter paper and the absorbance of the filtrate was read at 280 nm. Enzyme activities are expressed as µg tyrosine equivalents min$^{-1}$ ml$^{-1}$. Enzymic release of free α-amino groups from proteins was determined by a ninhydrin assay.

Activity versus locust cuticle was assayed as follows:
30 mg of ground locust cuticle (prepared using aqueous solutions of 1% potassium tetraborate) was vigorously shaken at 30° C. with 2 ml of enzyme, 4 ml of Britton-Robinson buffer at pH 5.0 and 0.05 ml of toluene. Samples (0.05 ml) were taken at intervals up to 24 hours incubation. Release of amino acids due to proteolytic activity was determined with ninhydrin.

The results are shown in Table 1.

Activity against nitroanilide substrates was assayed in reaction mixtures containing 0.1 ml enzyme solution and 1.8 ml Britton-Robinson buffer pH 8.0. After 3 min at 23° C. 0.1 ml substrate (in dimethylsulphoxide) was added and the reaction followed at 410 nm. Results are expressed as µmol nitroanilide released ml$^{-1}$ min$^{-1}$. An extinction coefficient of 8800 at 410 nm was used. The results are shown in Table 2.

All controls contained autoclaved enzyme (121° C. for 30 min) in place of unheated enzyme solutions.

b. Determination of molecular weight

Molecular weights were determined by SDS-polyacrylamide gel electrophoresis in neutral or alkali-gel systems and by gel filtration on Sephadex G-100 Fine in 0.15 M phosphate buffer. The results are shown in table 4.

TABLE 1

| Activity of Pr2 proteases towards proteins | | |
|---|---|---|
| | Protein | |
| Locust cuticle | Elastin | Hide protein azure |

| | | | |
|---|---|---|---|
| *M. anisopliae* ME 1* | + | − | + |
| *M. anisopliae* RS 23* | − | − | + |
| *M. anisopliae* RS 549* | − | − | + |
| *M. anisopliae* RS 298 | − | − | − |
| *M. anisopliae* RS 324 | − | − | − |
| *V. lecanii* 1 | − | − | − |

TABLE 1-continued

Activity of Pr2 proteases towards proteins

| | Protein | | |
|---|---|---|---|
| | Locust cuticle | Elastin | Hide protein azure |
| V. lecanii 2 | − | − | − |
| B. bassiana | − | − | − |
| A. aleyrodis | − | − | − |

+ activity detected
− no activity detected
*Comparison, not according to the invention

TABLE 2

Substrate specificities of Pr2 proteases

| | M. anisopliae | | | | | V. lecanii | V. lecanii | |
|---|---|---|---|---|---|---|---|---|
| Substrates | RS23* | RS549* | RS298 | RS324 | B. bassiana | 1 | 2 | A. aleyrodis |
| Bz-Phe-Val-Arg-NA | 66.7 | 66.7 | 100 | 100 | 100 | 100 | 100 | 100 |
| Bz-Val-Gly-Arg-NA | 83.3 | 55.6 | 7.6 | 0.1 | 0 | 0 | 0 | 0.1 |
| Bz-Pro-Phe-Arg-NA | 12.5 | 33.3 | 0.1 | 0.8 | 5.6 | 0 | 1.94 | 0.1 |
| CBZ-Gly-Pro-Arg-NA | 100 | 100 | 10.0 | 0.8 | 0.21 | 1.5 | 0.31 | 0.1 |
| Bz-Arg-NA | 0.7 | 0.1 | 0 | 0 | 0.1 | 0 | 0 | 0.1 |
| D-Val-Leu-Lys-NA | 54.2 | 0.1 | 0.5 | 0.3 | 0 | 0 | 0.78 | 0.1 |
| | (1.27) | (8.13) | (1.06) | (0.56) | (5.25) | (2.01) | (2.31) | (0.13) |

*Comparison, not according to the invention
Protease preparations after IEF were assayed at 23° C. in Britton-Robinson buffer (pH 8.0), 4% (v/v) dimethylsulphoxide, 0.06 mM substrate. Activities are expressed as % of maximum activity. Absolute values ($\mu$Mols NA min$^{-1}$ml$^{-1}$ per mg protein) corresponding to 100% are given in parenthesis. The enzymes showed no activity or trace activity (<0.1%) against Suc-(Ala)$_2$-Pro-Phe-NA, Suc-Phe-Leu-Phe-NA, Suc-(Ala)$_2$-Pro-Abu-NA, Suc-(Ala)$_2$-Val-Ala-NA or Ac-(Ala)$_3$-NA. M. anisopliae ME1 protease Pr2 has a similar specificity to RS 23 and RS 549.

TABLE 3

The effect of inhibitors on Pr2 activity

| | M. anisopliae | | | | | | V. lecanii | |
|---|---|---|---|---|---|---|---|---|
| | ME1 | RS23 | RS549 | RS298 | RS324 | B. bassiana | 1 | 2 |
| PMSF (0.2 mM) | 7.0 | 27.6 | 33.3 | 2.5 | 1.7 | 0.1 | 0.1 | 0.1 |
| TOS-Lys-CH$_2$Cl (0.05 mM) | 46.6 | 35.7 | 14.7 | 100 | 100 | 87.5 | 87.5 | 100 |
| Leupeptin (50 $\mu$ml$^{-1}$) | 5.6 | 0.12 | 12.27 | 66.7 | 0.34 | 20.0 | 0.4 | 68.8 |
| Antipain (50 $\mu$ml$^{-1}$) | — | 0.1 | 13.3 | 95.0 | 62.5 | 60.0 | 41.7 | 94.4 |
| Soya bean trypsin inhibitor (50 $\mu$ml$^{-1}$) | 0.1 | 0.1 | 26.7 | 100 | 100 | 89.1 | 100 | 100 |
| N-Ethylmaleimide (1 mM) | 97.0 | 100 | 100 | 100 | 100 | 100 | 100 | 100 |
| TOS-Phe-CH$_2$Cl (0.05 mM) | 100 | 100 | 100 | 100 | 100 | 100 | 100 | 100 |
| BOC-Gly-Leu-Phe-CH$_2$Cl (0.05 mM) | 100 | 100 | 100 | 100 | 100 | 100 | 100 | 100 |
| Turkey egg white inhibitor (50 $\mu$ml$^{-1}$) | 100 | 100 | 100 | 100 | 100 | 100 | 100 | 100 |
| Hirudin (20 $\mu$ml$^{-1}$) | — | 100 | 100 | 100 | 100 | 100 | 100 | 100 |

*Comparison, not according to the invention
Note:
The enzymes were preincubated with each inhibitor in Britton-Robinson buffer (pH 8.0) at 25° C. for 15 min before assaying with Bz-Phe-Val-Arg-NA. Activities are expressed as a % of the control activity.

TABLE 4

Physical parameters of Pr2 proteases

| | Isoelectric point (pI) |
|---|---|
| M. anisopliae ME 1* | 4.4 |
| M. anisopliae RS 23* | 5.0 |
| M. anisopliae RS 549* | 6.0 |
| M. anisopliae RS 298 | 5.8 |
| M. anisopliae RS 324 | 5.8 |
| V. lecanii 1 | 5.6 |
| V. lecanii 2 | 5.6 |
| B. bassiana | 7.4 |
| A. aleyrodis | 4.8 |

Molecular weights of all enzymes: 25000–30000.
Optimum pH for activity: 8.0 (except ME1 which is 9.0).
Optimum pH for stability: 6.0–9.0.
Temperature stability: stable at temperatures up to 50° C. (10 min at pH 8.0).
*Comparison, not according to the invention.

We claim:

1. An enzyme preparation comprising at least one protease derived from an entomopathogenic strain of a fungus belonging to one of the following species: *Metarhizium anisopliae, Beauveria bassiana, Verticillium lecanii* and *Aschersonia aleyrodis*, and characterized by the following properties:

(a) substantially no activity against hide protein azure, locust cuticle and elastin;
   (b) specificity for Bz-Phe-Val-Arg-NA; and
   (c) not inhibited by soybean trypsin inhibitor.

2. An enzyme preparation according to claim 1 in which the protease is derived from one of the following strains, or a derivative or mutant thereof capable of producing said protease: CMI 319793, CMI 319794, CMI 319795, CMI 319796, CMI 319797 and CMI 319798.

3. An enzyme preparation according to claim 1, in which the protease has a molecular weight of 25000 to 30000, an optimum pH for activity of about 8.0, an optimum pH for stability of 6.0 to 9.0, and is stable at temperatures up to 50° C.

* * * * *